United States Patent [19]
Dent et al.

[11] Patent Number: 6,147,107
[45] Date of Patent: Nov. 14, 2000

[54] SPECIFIC INHIBITION OF THE P42/44 MITOGEN ACTIVATED PROTEIN (MAP) KINASE CASCADE SENSITIZES TUMOR CELLS

[75] Inventors: Paul Dent, Glen Allen; Steven Grant; W. David Jarvis, both of Richmond, all of Va.

[73] Assignee: Virginia Commonwealth University, Richmond, Va.

[21] Appl. No.: 09/203,342

[22] Filed: Dec. 20, 1998

[51] Int. Cl.$^7$ .......................... A01N 43/02; A61K 31/335
[52] U.S. Cl. ............................................. 514/449; 514/619
[58] Field of Search ..................................... 514/619, 449

[56] References Cited

FOREIGN PATENT DOCUMENTS

WO 97/40842   11/1997   WIPO .

OTHER PUBLICATIONS

Jarvis et al. "Evidence for Involvement of Mitogen Activated Protein Kinase, Rather than Stress Activated Protein Kinase, in Potentiation of 1–α–D–Arabinofuransylcytosine–induced apoptosis by Interruption of Protein Kinase C signalling" *Molecular Pharmacology* 54:844–856 (1998).

Wang et al., "Bryostatin 1 enchances paclitaxel–induced mitochondrial dysfunction and apoptosis in human leukemia cells (U937) ectopically expressing Bcl–XI" *Leukemia* 13:1564–1573 (1999).

Kavanaugh et al., "Calcium Dependent Stimulation of Mitogen Activated Protein Kinase Activity in A431 Cells by Low Doses of Ionizing Radiation" *Radiation Research* 149:579–587 (1998).

Favata, M. F., et al., "Identification of a Novel Inhibitor of Mitogen– activated Protein Kinase Kinase", The Journal of Biological Chemistry, vol. 273, No. 29, Issue of Jul. 17, pp. 18623–18632, 1998.

Dent, P., et al., Review: "The roles of signaling by the p24/44 mitogen– activated protein(MAP) kinase pathway", Leukemia (1998) 12.

Carter, S. et al., "Inhibition of the mitogen activated protein (MAP) kinase cascade potentiates cell killing low dose ionizing radiation in A432 human squamous carcinoma cells", Oncogene (1998) 15.

Alessi, et al., "PD 098059 Is a Specific Inhibitor of the Activation of Mitogen–activated Portein Kinase Kinase in Vitro and in Vivo", vol. 270, No. 46, Issue of Nov. 17, 1995, pp. 27489–27494.

*Primary Examiner*—Dwayne C. Jones
*Attorney, Agent, or Firm*—McGuire, Woods, Battle & Boothe, LLP

[57] ABSTRACT

Mammaliam cancer cells are effectively killed when treated with a lethal agent (e.g. radiation or chemotherapeutic agents) in combination with an inhibitor specific for the p42/44 MAP kinase cascade "proper".

20 Claims, 10 Drawing Sheets

SPECIFIC INHIBITION OF THE P42/44 MITOGEN ACTIVATED PROTEIN (MAP) KINASE CASCADE SENSITIZES TUMOR CELLS

CROSS-REFERENCE TO RELATED APPLICATIONS

This patent application is a continuation-in-part (CIP) application of both the provisional application filed Oct. 21, 1998 which is entitled SPECIFIC INHIBITOR OF THE P42/44 MITOGEN ACTIVATED PROTEIN (MAP) KINASE CASCADE RADIOSENSITIZES TUMOR CELLS TO CLINICALLY RELEVANT LOW DOSE IONIZING RADIATION and the provisional application filed Oct. 7, 1998 having Ser. No. 60/103357 which is entitled CHEMOPOTENTIATION BY INHIBITION OF THE MAPK PATHWAY. The complete contents of these appilcations is herein incorporated by reference.

This invention was made using funds from grants from the National Institutes of Health having a grant number RO1-CA63753. The government may have certain rights in this invention.

BACKGROUND OF THE INVENTION

1. Field of the Invention

The invention is directed toward the treatment of cancer in mammals and, more particularly, to the enhancement of the clinical efficacy of traditional radiation, chemotherapy, and other techniques by the administration of specific inhibitors of the MAP kinase cascade.

2. Background of the Invention

Radiation therapy is, in many cases, the therapy of choice for the treatment of cancers, including esophogeal, mammary, head and neck, brain, prostate and certain leukemias. However, it is well-known that incomplete killing of neoplastic cells can result in the recurrance of cancer even after rigourous radiation treatment regimens are completed. Indeed, there are suggestions that some cell populations are stimulated to proliferate as a result of exposure to radiation, thus completely defeating the purpose of the treatment. Clearly, the need for more efficient methods to kill neoplastic cells persists, and a method to eliminate the occurance of cellular proliferation in response to radiation therapy would be highly beneficial.

In addition, severe side effects are often associated with radiation therapy, including fibrosis, mucocitis, leukopenia and nausea. The development of radiation therapy methods which utilize fewer exposures to radiation, or lower doses per exposure, or both, and yet which still achieve the same or enhanced levels of anti-neoplastic activity, would be highly advantageous.

Chemotherapy is also a mainstay of cancer treatment and is routinely used with success against many types of cancer. Nevertheless, certain types of cancer are not amenable to chemotherapy protocols which are currently in use. Some types of tumors simply do not respond to standard methods of chemotherapy, or respond for a time and later become insensitive, resulting in a recurrance of the cancer. New methods that enhance current chemotherapy protocols are highly desirable.

The molecular mechanism(s) by which tumor cells are killed, survive or are stimulated to proliferate after exposure to ionizing radiation are not fully understood. Several reports have demonstrated that radiation activates multiple signaling pathways within cells in vitro which can lead to either increased cell death or increased proliferation depending upon the dose and culture conditions. [Verheij et al. (1996) *Nature*, 380, 75–79; Rosette and Karin (1996) *Science* 274, 1194–1197; Chmura et al. (1997) *Cancer Res.* 57, 1270–1275; Santana et al. (1996) *Cell* 86, 189–199; Kyriakis and Avruch (1996) *Bioessays* 18, 567–577; Xia et al. (1995) *Science* 270, 1326–1331; Kasid et al. (1996) *Nature* 382, 813–816]. It has been shown that radiation-mediated activation of acidic sphingomyelinase generates ceramide and subsequently activates the Stress Activated Protein (SAP) kinase pathway (sometimes referred to in the literature as the c-Jun $NH_2$-terminal kinase (JNK) pathway). This pathway has been proposed to play a major role in the initiation of apoptosis (cell death) by radiation (Verheij et al.; Rosette et al.; Chmura et al.; Santana et al.; Kyriakis and Avruch; Xia et al.).

Likewise, the molecular mechanisms of the action of chemotherapy agents are not well-understood, particularly those processes involving specific signaling systems that impinge upon cell survival. For example, numerous signaling responses are associated with the action of the chemotherapeutic agent 1-[β-D-arabinofuranosyl] cytosine hydrochloride (ara-C). These include: formation of the lipid messengers diglyceride [Kucera and Capizzi (1992) *Cancer Res.* 52, 3886–3891; Strum et al. (1994) *J. Biol. Chem.* 269, 5493–5497] and ceramide [Strum et al. (1994)]; and activation of protein kinase C (PKC) [Kharbanda et al. (1991) *Biochemistry* 30, 7747–7752; Riva et al. (1995) *Anticancer Res.* 15, 1297–1302], the p42/44 mitogen activated protein (p42/44 MAP) kinase cascade [Kharbanda et al. (1994) *Mol. Pharmacol.* 46, 67–72] and the SAP kinase [Saleen et al. (1995) *Cell Growth Diff.* 6, 1651–1658] pathway.

Experimentation has been directed toward elucidating the means by which cells survive (or even proliferate) in response to radiation exposure and chemotherapy. For example, it has been demonstrated the the antileukemic influence of ara-C is substantially augmented by pharmacological reductions in Protein Kinase C (PKC) activity [Grant et al. (1994) *Oncology Res.* 6, 87-99].

There are two potential protective pathways downstream of PKC: the P13 kinase pathway and the p42/44 MAP kinase pathway (Pathway 1 below). The interplay (if any) of the two pathways and their roles with respect to cellular responses to lethal agents such as radiation and chemotherapy are the subject of intense investigation and debate. Most studies have focussed on the role of the P13 pathway and these studies have shown that inhibition of P13 kinase causes apoptosis in many cell types.

Activation of the p42/44 MAP kinase cascade has been suggested to be cytoprotective versus both UV/ionizing radiation and drug treatments [Xia et al., (1995); Jarvis et al. (1997) *FEBS Lett.* 112, 9–14; Jarvis et al.(1997) *Mol. Pharm.*52, 935–947; Canman et al. (1995) *Genes Dev.* 9, 600–611]. Several studies have also sugested that the MAP and SAP kinase pathways may be coordinately regulated: the degree to which each is activated by a stimulus may determine the cellular fate toward differentiation, proliferation or death [Rosette et al. (1996); Kyriakis and Avruch (1996); Xia et al. (1995); Spector et al. (1997); Jarvis et al. (1997b); Cuenda et al. (1995) *FEBS Lett.* 364, 229–233].

With respect to the cellular response to ionizing radiation, another cellular target has been proposed to be involved. The epidermal growth factor (EGF) receptor has been shown to be activated in a dose dependent fashion in response to radiation [Schmidt-Ullrich et al. (1996) *Radiation Research,* 145, 81–85; Schmidt-Ullrich et al. (1997) *Oncogene* 15, 1191–1197]. Activation of the EGF receptor in turn activates the p42/44 MAP kinase cascade (Schmidt-Ullrich et al. 1997).

Other signal transduction pathways exist which are known to be downstream effectors of both sphingomyelinase ceramide and EGF receptor signaling. The p38-RK cascade has been described in mammalian cells as a pathway activated in response to hyper-osmotic stress, and was recently shown to be activated in response to ceramide treatment of U937 monoblasts [Jarvis et al, 1997b; Cuenda et al.(1995) *FEBS Lett.*364, 229–233] The $p70^{S6\ kinase}$ and glycogen synthase kinase 3 (GSK3) are downstream effectors of PK-B/c-Akt and P13 kinase [Alessi et al (1996) *J. Biol. Chem.* 270, 27489–27494; Cross et al. (1995) *Nature* 378, 785–789] P13 kinase itself is a downstream effector of the EGF receptor, and was recently suggested to be activated in response to ultraviolet irradiation of cells [Kulik et al. (1997) *Mol. Cell. Biol.* 17, 1595–1606]. However, the ability of ionizing radiation to modulate the activities of these protein kinases had not been demonstrated until Carter et al. [(1998) *Oncogene*, 16, 2787–2796].

Activation of the p42/44 MAP kinase cascade in response to growth factors has been shown to be involved in both differentiation and proliferative responses of cells depending upon both the cell type examined and the amount of p42/44 MAP kinase activation [Kolch et al. (1991) *Nature* 349, 426–428; Dent et al. (1992) *Science* 275, 1404–1407; Pumiglia and Decker (1997) *Proc. Natl. Acad. Sci.*94, 448–452; Wixler et al. (1996) *FEBS Lett.* 385, 131–137; Traverse et al. (1994) *Curr. Biol.* 4, 694–701; Whalen et al. (1997) *Mol. Cell. Biol.* 17, 1947–1958]. Acute activation of the MAP kinase cascade by growth factors has been shown to potentiate proliferation, whereas chronic elevation of MAP kinase activity has been demonstrated to be cytoprotective against irradiation (Canman et al. 1995) and to inhibit DNA synthesis potentially via induction of the cyclin dependent kinase (cdk) inhibitor protein $p21^{Cip-1}$. [Pumiglia and Decker (1997); Wixler et al. (1996); Traverse et al. (1994); Whalen et al. (1997); Lloyd et al. (1997) *Genes and Dev.* 11, 663–677; Fan et al. (1995) *J. Cell. Biol.* 131, 235–242; Missero et al. (1996) *Genes and Dev.* 10, 3065–3075; Macloed et al. (1995) *Genes and Dev.* 9, 935–944; Liu et al (1996) *Cancer Res.* 56, 31–35; Deng et al. (1995) *Cell* 82, 675–684] The cdk inhibitor protein $p21^{Cip-1}$ can also be induced in response to radiation exposure of cells, and cultured fibroblasts from $p21^{Cip-1}$ 'knock-out' mice which cannot express $p21^{Cip-1}$ have been shown to be more radiosensitive than wild type cells, demonstrating that expression of this molecule is cytoprotective against radiation [Missero et al. (1996); Macloed et al. (1995); Liu et al (1996); Deng et al. (1995)] The mechanism by which $p21^{Cip-1}$ is induced in response to irradiation of cells has been proposed to be via the function of p53 which is able 10 to sense DNA damage, and not by p42/44 MAP kinase signaling. This data would appear to preclude signaling via the p42/44 MAP kinase cascade as a player in the radiation-mediated induction of $p21^{Cip-1}$ [Missero et al. (1996); Macloed et al. (1995); Liu et al (1996); Deng et al. (1995); Van den Heuvel and Harlow (1993) *Science* 262, 2050–2054; Lees et al (1993) *Oncogene* 8, 1593–1602; Brugarolas eta 1. (1995) *Nature* 377, 552–557; Freemerman et al. (1997) *Leukemia* 11, 504–513; Akiyarna et al. (1997) *Cancer Res.* 57, 57, 1495–1501; Mothersill et al (1995) *Radiation Res.* 142–181–187; Bernhard et al (1995) *Radiation Environ. Biophys.* 34, 79–83; Muschel et al (1997) *Vitam. Horm.* 53, 1–25; Johnson et al. (1994) *Mol. Carcinogenesis* 11, 59–64; Michieli et al. (1994) *Cancer Res.* 54, 3391–3395].

However, other reports [Carter et al. (1998)] have demonstrated radiation induction of $p21^{Cip-1}$ in a MAP kinase dependent fashion in cells which express non-functional p53.

SUMMARY OF THE INVENTION

It is an object of this invention to provide a method to kill cancer cells, comprised of exposing the cancer cells to an inhibitor that is specific for the p42/44 MAP kinase cascade proper in combination with a lethal agent. It is a further object of this invention to provide a method to treat cancer in mammals. That method will encompass administering, in combination with a lethal agent (e.g. ionizing radiation, chemotherapeutic agents, heat, ultraviolet light, high intensity red light as used in photo-dynamic therapy, etc.) together with inhibitors specific for the function of the p42/44 MAP kinase cascade proper. These inhibitors may act at any site within the cascade proper to inhibit cascade function. It is a further object of this invention to use 2'-amino-3'-methoxy-flavone (PD-98059, Alessi et al., 1995, *J. Biol. Chem.* 270, 27489–27494), PD184352 (see structure below), 1,4-diamino-2,3-dicyano-1,4-bis[2-aminophenylthio]butadiene (U0126, Favata et al., 1998, *J. Biol. Chem.*, 273, 18623–18632 ), SL327 or SW073 (the latter two compounds are proprietary compounds provided to Dr. Dent by the DuPont Pharmaceutical Company, Inc.) or similar compounds which specifically inhibit the function of the p42/44 MAP kinase cascade proper. These compounds may act by inhibiting the ability of Raf protein kinases to phosphorylate MEK1 and MEK2 (as we have demonstrated with PD98059, U0126, SL327) or by inhibiting other steps within the MAP kinase cascade proper, in order to treat cancer in mammals. The administration of such an inhibitor will potentiate the ability of radiation or chemotherapy, or both, or of other lethal agents, to cause apoptosis of cancer cells, thus decreasing cancer recurrences.

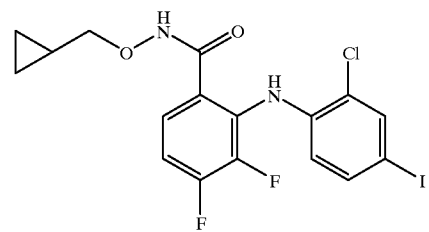

PD184352

MTT assays were carried out as described in Methods and Example 1 below.

Figure 6:
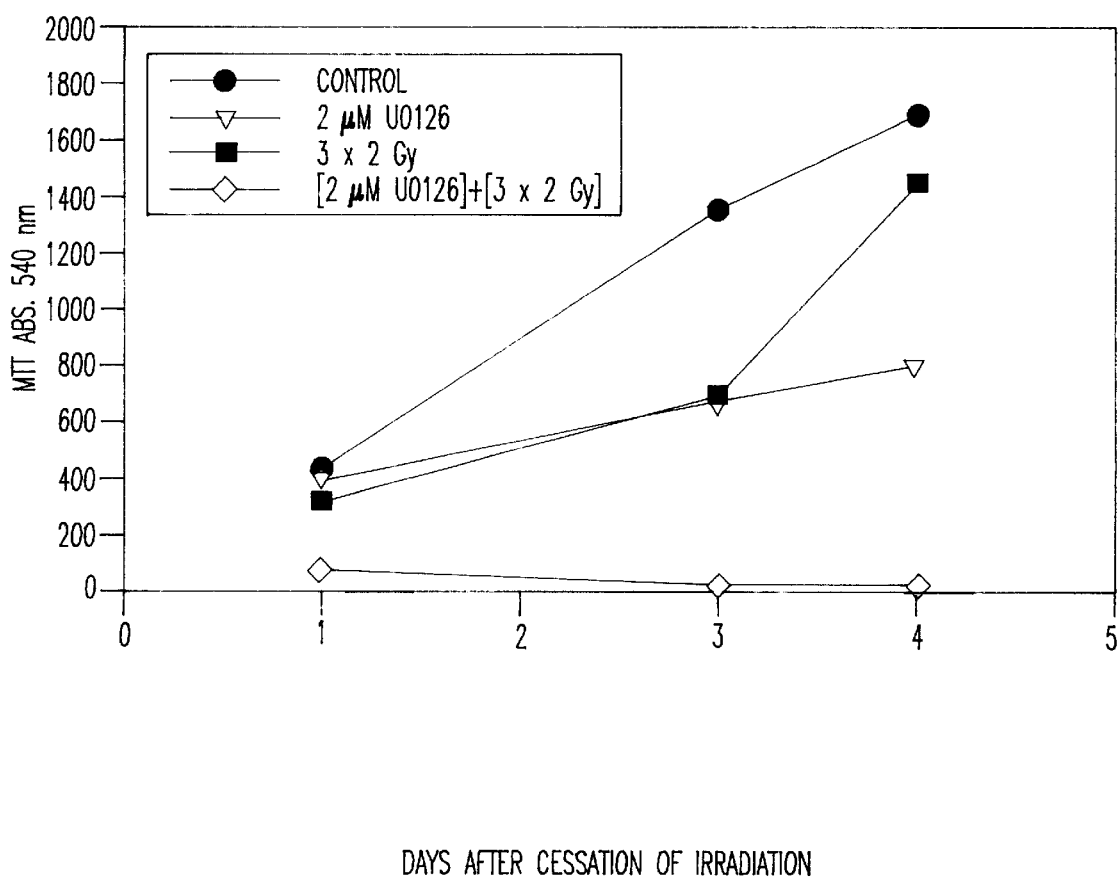

FIG. 6. Decreased proliferative rate of MDA-MB-231 mammary cancer cells in MTT assays over 3–4 days wherein cells were treated with radiation (3×2 Gy) alone, 2 μM U0126 alone, or radiation plus U0126. Control cells were treated with vehicle (DMSO). MTT assays were carried out as described in Methods and Example 1 below.

Figure 7:
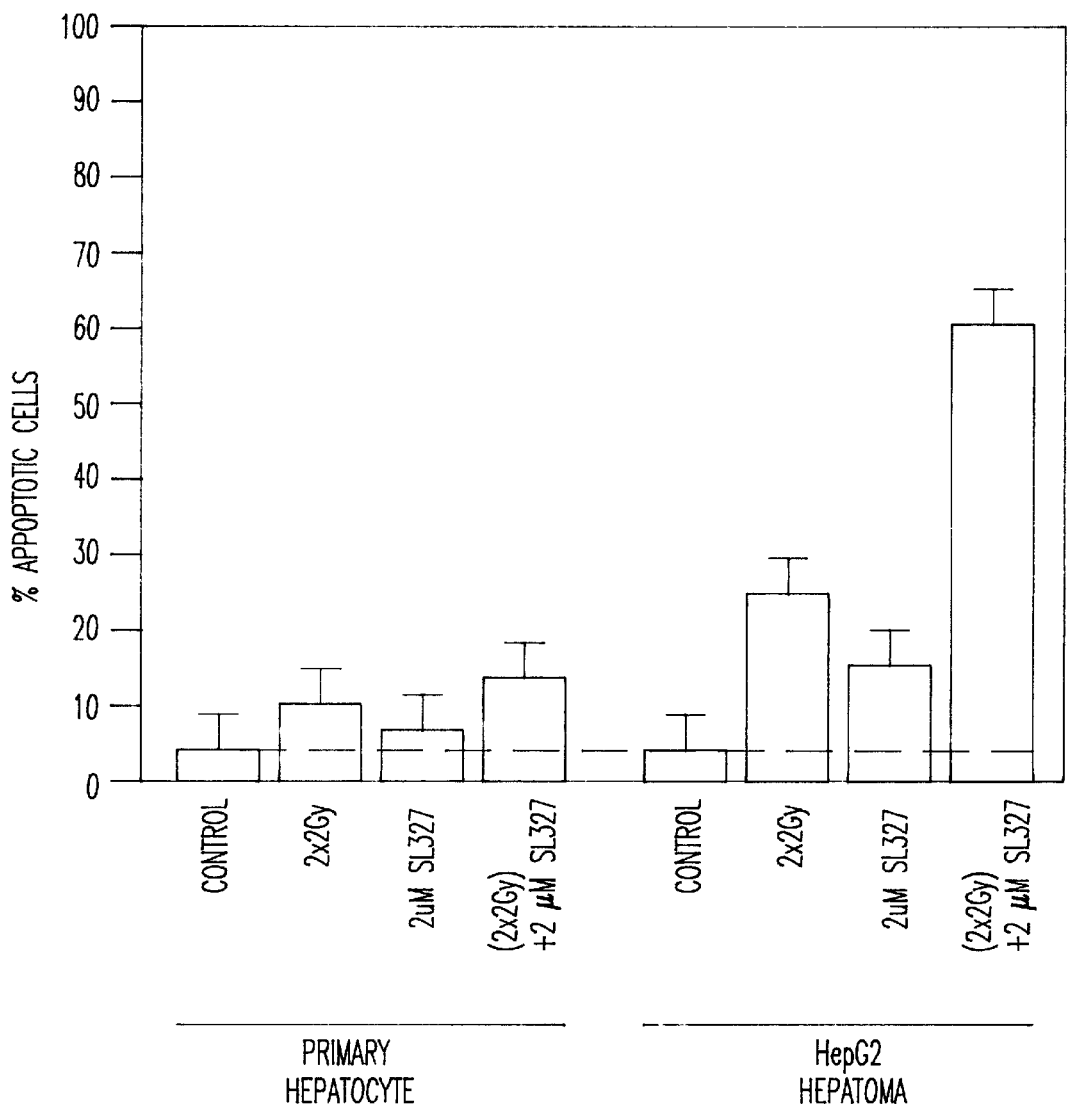

FIG. 7. TUNEL assays to compare the apoptosis response of primary hepatocyte versus HepG2 hepatoma cells. Control cells were untreated.

Experimental cells were exposed to radiation (2×2 Gy), or treated with the p42/44 MAP kinase inhibitory drug SL327 (2 μM), or treated with SL327 and exposed to radiation. Twelve hours after the final irradiation, cells were assessed by the TUNEL assay.

Figure 8:
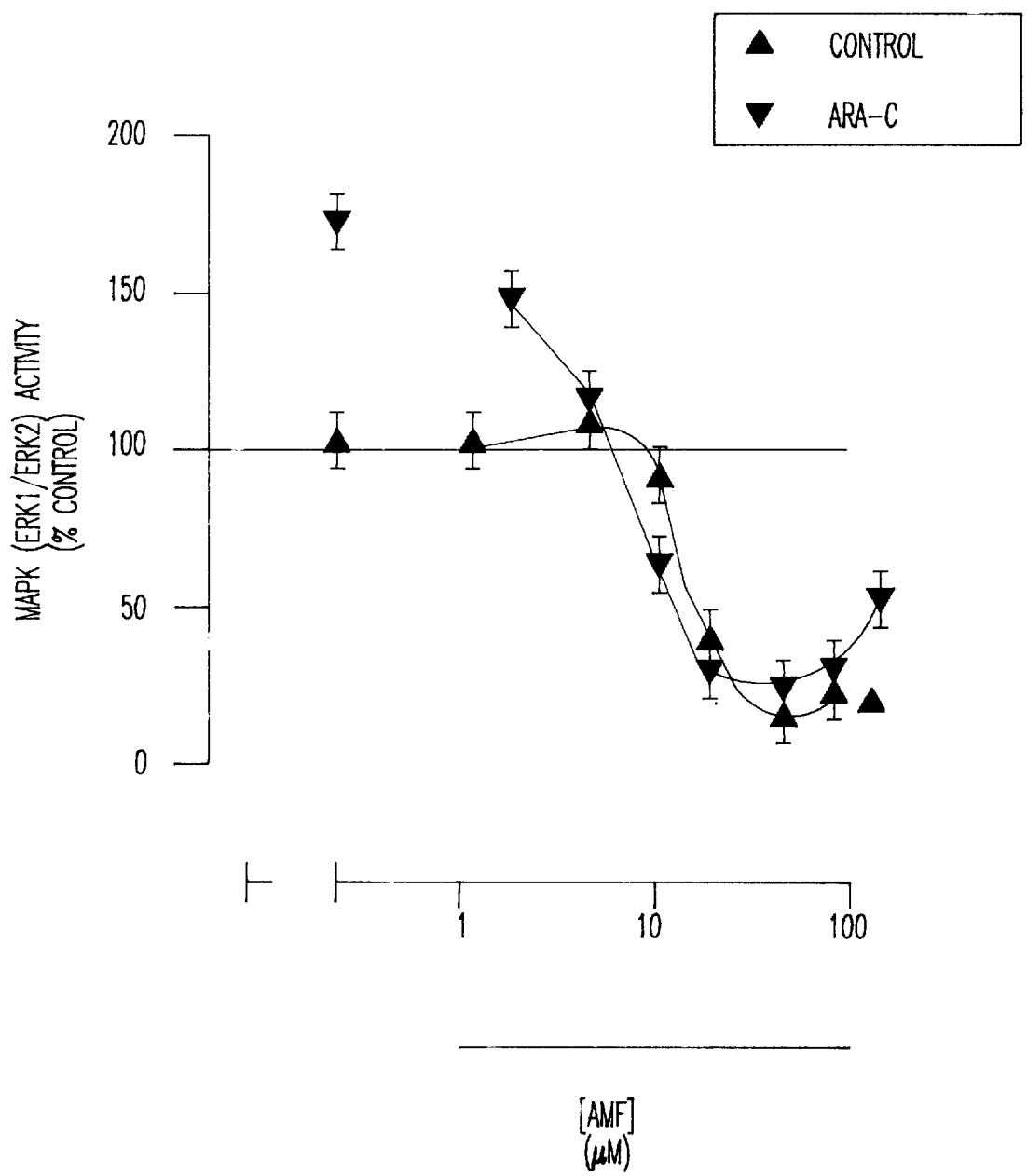

FIG. 8. Suppression of MAP kinase activity by PD98059. HL-60 cells were exposed to ara-C (10 μM) in the absence or presence of aminomethoxyflavone (PD98059; 2.5 μM) for 3 hours. MAP kinase activity (p42-ERK1/p44-ERK2) was determined by in vitro assay. In each case, values reflect the mean ±SE of duplicate determinations, and are expressed as a percentage of basal activity present in untreated controls. Data shown are from a representative study performed three times with comparable results.

Figure 9:
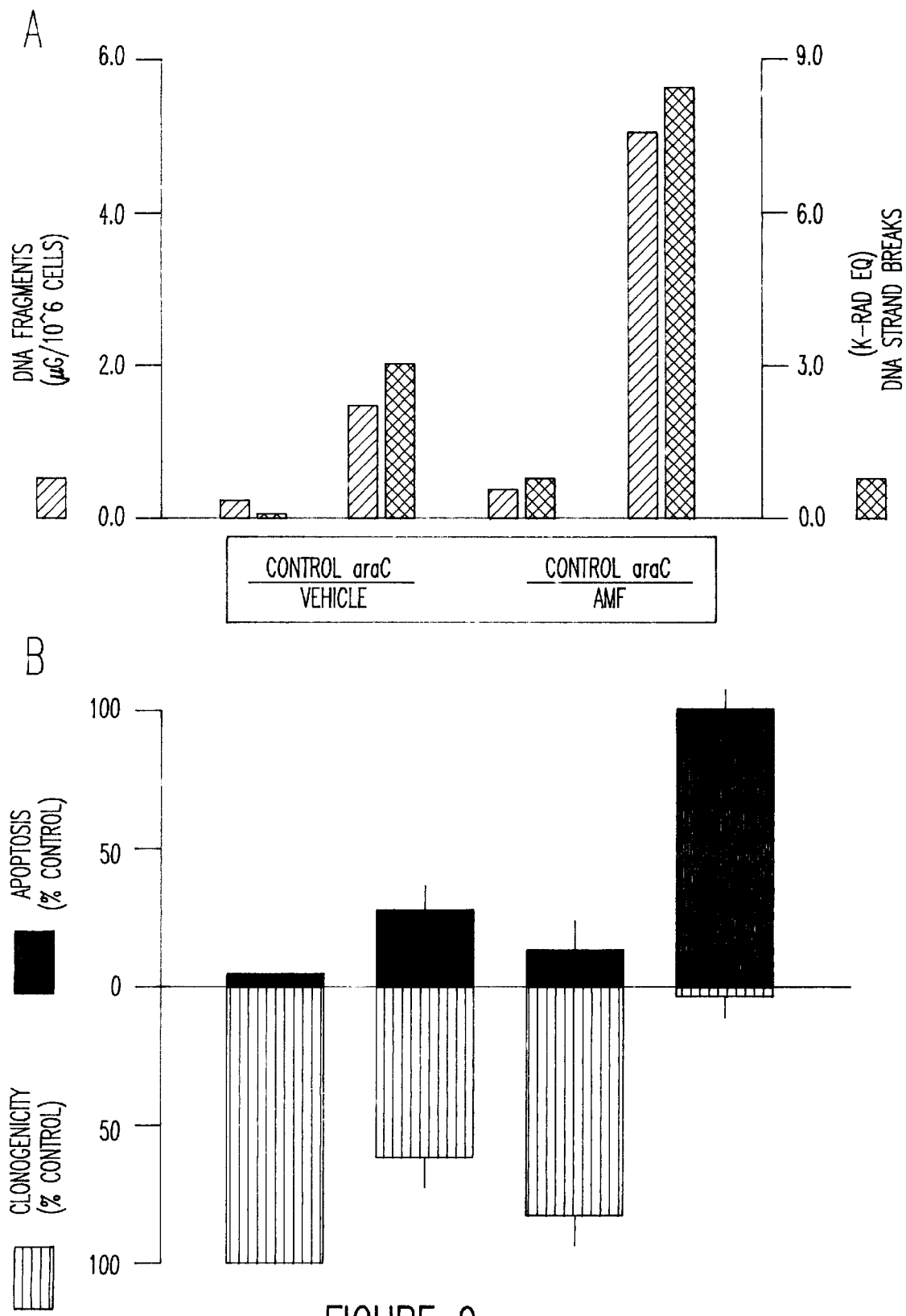

FIGS. 9a and 9b. Potentiation of ara-C-induced apoptosis by PD98059. HL-60 cells were exposed to ara-C (10 μM) in the absence or presence of aminomethoxyflavone (PD98059; 2.5 μM) for 6 hours. Apoptotic DNA damage and cell death were assessed as described in Methods. FIG. 9a. shows accumulation of double-stranded DNA fragments (single hatched bars) and occurance of double-stranded breakage of bulk DNA (double hatched bars); for both measurements, values represent the mean ±SEM of quadruplicate determinations. FIG. 9b. Shows induction of apoptosis (lined bars) and suppression of clonogenicity (solid bars); values represent the mean ±SEM of triplicate determinations. Data shown are from a representative study performed four times with comparable results.

Figure 10:
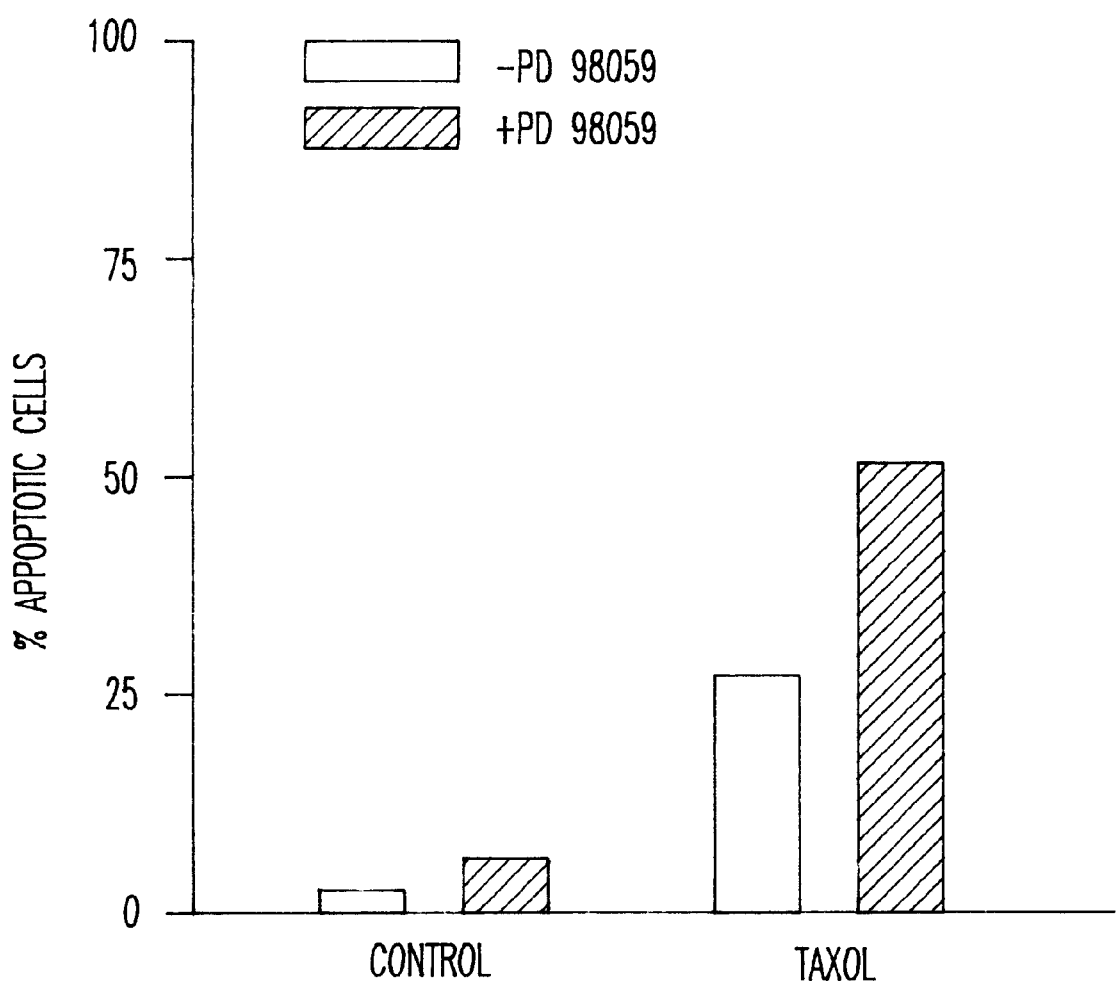

FIG. 10. Effect of PD98059 on taxol mediated apoptosis. Cells were exposed to taxol (0.5 μM; 6 hours) in the presence or absence of 10 μM PD98059. At the end of the incubation period, the percentage of apoptotic cells was determined as described below. Results represent the means ±SD for three separate experiments.

DETAILED DESCRIPTION OF THE PREFERRED EMBODIMENTS OF THE INVENTION

Experiments were conducted to test whether radiation induced activation of the p42/44 MAP kinase cascade is cytoprotective against radiation-induced cell killing in carcinoma cells. Previous studies had used high radiation doses (~5–15 Gy). In contrast, these experiments tested the effects of clinically relevant low radiation doses (~1–2 Gy). Carcinoma cells were irradiated with low doses 15 of γ-rays in the presence or absence of p42/44 MAP kinase cascade blockade using the MEK1/2 inhibitor PD98059 [Alessi et al. (1995)] and the subsequent activations of signal transduction pathways and cell viability were examined.

Similarly, the functional relationships between these signaling pathways with respect to their contribution to the cytotoxicity of chemotherapeutic agents were examined. Those studies were carried out with HL-60 promyelocytic leukemia cells in the presence and absence of chemotherapeutic agents with and without concomitant exposure to the MEK1/2 inhibitor PD98059.

In the Examples described below, we demonstrate that the p42/44 MAP kinase cascade proper is a key cytoprotective pathway that is activated in response to clinically relevant doses of ionizing radiation and chemotherapy. The Examples document that specific inhibitors of the MAP kinase cascade proper enhance the ability of radiation and to induce apoptosis in cancer cells, and that the effect is specific for rapidly growing cells. Likewise, the apoptotic action of chemotherapeutic agents is dramatically enhanced by pharmacologic disruption of the p42/44 MAP kinase cascade proper. As a result of these observations, we have devised a novel method for the treatment of cancer which involves the administration of specific inhibitors of the p42/44 MAP kinase cascade in combination with a lethal agent such as radiation therapy or chemotherapy.

The cytoprotective p42/44 MAP kinase cascade is outlined in Pathway 1 below. The cascade is composed of seven steps which finally lead to the entrance of the effector molecule p90 ribosomal S6 kinase (RSK) into the nucleus of the cell. RSK subsequently initiates nuclear events which lead to cell survival. While all of the molecules listed are part of the MAP kinase cascade, the first three (above the line) are also part of several other signal transduction cascades. In contrast, the last four molecules (below the line) are specific for the p42/44 MAP kinase cell-protective cascade, and constitute the p42/44 MAP kinase cascade "proper".

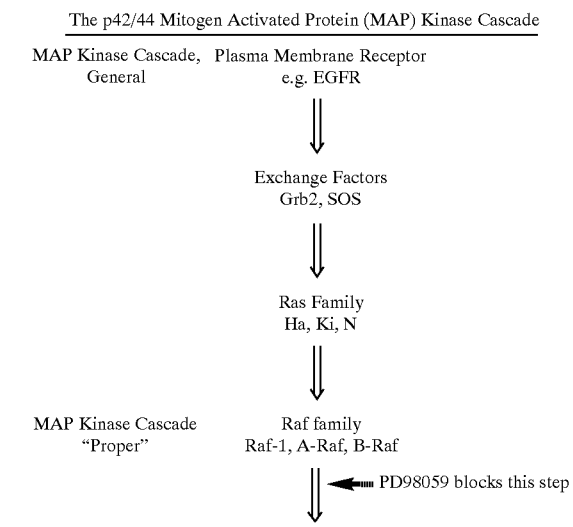

The p42/44 Mitogen Activated Protein (MAP) Kinase Cascade

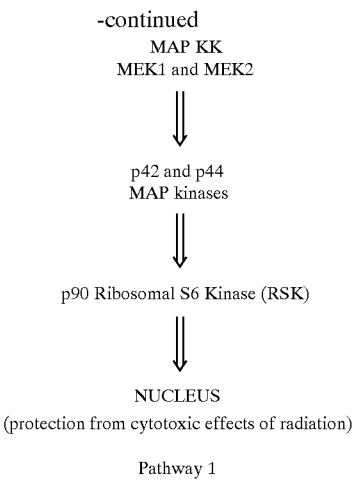

-continued
MAP KK
MEK1 and MEK2
⇓
p42 and p44
MAP kinases
⇓
p90 Ribosomal S6 Kinase (RSK)
⇓
NUCLEUS
(protection from cytotoxic effects of radiation)

Pathway 1

It has previously been proposed to use inhibitors of the enzyme Protein Kinase C (PKC) for cancer therapy (see U.S. Pat. No. 5,552,391). Also, it has been proposed to use inhibitors of PKC isoforms in combination with oncolytic agents and radiation therapy in order to enhance the clinical efficacy of those therapies (see WO 97/40842 to Jirousek, et al.). Those proposals came in the wake of the discovery that the use of PKC inhibitors augments the apoptotic effect of radiation on cancer cells in vitro. Use of these inhibitors as drugs is, however, problematic.

PKC is known to be a major player in cell signaling, but its exact role is still a subject of intense debate. The story is highly complex in that PKC exists as several isoforms which have been denominated "classical", "atypical" and "novel". The exact roles of the PKC isoforms are also a matter of intense study and debate. With respect to the MAP kinase cascade, some research groups believe that PKCs directly phosphorylate and activate Raf-1. Others claim that PKCs act upstream and can activate the Ras family of proteins. Still others claim that PKCs activate the JNK, p38 and P13 kinase pathways, which are involved in apoptosis. Concensus with respect to PKC function has not been arrived at and the literature is huge and often conflicting. What is clear is that PKCs have multiple targets and are not specific for the cytoprotective MAP kinase cascade proper.

Thus, one obvious drawback to the use of PKC inhibitors as drugs is the lack of specificity of their target molecules. Prediction and causal analysis of the outcome of treatment regimens involving PKC inhibitors are complicated, if not rendered impossible, due to the inherent lack of specificity.

In contrast, the inhibitors which are to be used in the claimed invention inhibit only the MAP kinase cascade proper. That is, the inhibitors are "specific" for the p42/44 MAP kinase cascade proper. Thus, according to the claimed invention, a compound which is known to be a specific inhibitor for the MAP kinase cascade proper is administered to the patient in combination with treatment by conventional radiation or chemotherapy, or both, or with an alternative lethal agent (e.g. heat, UV radiation, magnetic or electric fields, pH altering agents, etc.) for the purpose of enhancing the clinical efficacy of the lethal agent.

One aspect of the present invention contemplates administering to a patient a MAP kinase cascade specific inhibitor in combination with administering to the patient an acceptable chemotherapeutic agent or combination of agents. As used herein "chemotherapeutic agent" means any chemical agent or drug used in chemotherapy treatment which selectively affects tumor cells, including but not limited to such agents as taxanes, adriamycin, amscrine, etoposide, cisplatinum, vincristine, vinblastine and methotrexate. Other such agents are well-known in the art. It is anticipated that the MAP kinase cascade inhibitor may be administered either in combination with or separately from the chemotherapeutic agent(s). The dose will vary depending on a variety of factors including the route of administration, choice of chemotherapeutic agent, etc.

Another aspect of the present invention is to administer p42/44 MAP kinase cascade specific inhibitors in combination with treating the patient by exposing the patient to ionizing radiation. The protocols for traditional radiation therapy, e.g. γ-radiation, are known, readily available, and routinely practiced by those of skill in the art. These include established protocols for the administration of drugs in combination with radiation therapy [Wobst et al. (1998) Ann. Oncol. 9, 951–962). The dose of ionizing radiation will vary depending on a variety of factors including intensity, source of radiation, etc.

The invention contemplates the use of an inhibitor specific for the MAP kinase cascade proper. Several specific inhibitors are known and would be appropriate candidates for formulation. PD98059 (2'-amino-3'-methoxy-flavone) and U0126 (1,4-diamino-2,3-dicyano-1,4-bis[2-aminophenylthio] butadiene) are commercially available as crystalline solids. PD184352 is under commercial development and its structure is noted above. Compounds SL327 and SW073 are at present proprietary in nature. These five inhibitors act by inhibiting the ability of the Raf protein kinases to phosphorylate and activate the MEK1/2 protein complex. Their mode of action is to bind to MEK1/2 and sterically prevent Raf from binding. Raf is thus prohibited from phosphorylating and activating MEK1/2, which is in turn prevented from activating p42/44 MAP kinase. This in turn precludes the activation of transcription factors in the nucleus which might otherwise promote cell survival. Although these five inhibitors act specifically at the level of MEK1/2, it is understood that inhibitors of any level of the MAP kinase cascade proper (shown in Pathway 1) may be utilized.

Administration of the inhibitor may be, for example, prior to, after, or concurrent with radiation or chemotherapy treatment, or both. One skilled in the art will recognize that the amount of specific MAP kinase inhibitor to be administered will be that amount sufficient to enhance the antineoplastic effect of the radiation and/or chemotherapy. Such an amount may vary inter alia depending on the gender, age, weight and condition of the patient, and must be determined on a case by case basis. The amount may vary according to the size and type of neoplasia, as well as the particular radiation or chemotherapy protocol which is followed. Generally, a suitable dose is one that results in a concentration of the inhibitor at the site of the tumor in the range of 0.5 nM to 200 μM, and more usually from 20 nM to 80 nM. It is expected that serum concentrations for 40 nM to 150 nM should be sufficient in most cases. Administration may be oral, perenteral or topical, and is likely to be oral or intravenous. The inhibitor may be administered in any of several forms, including tablets, pills, powders, lozenges, sachets, cachets, elixirs, suspensions, emulsions, solutions, syrups, aerosol (as a solid or in a liquid medium), soft or hard gelatin capsules, suppositories, sterile injectable solutions and sterile packaged powders for either oral or topical application.

The inhibitor may be administered as a composition which also includes a pharmaceutically acceptable carrier.

The inhibitor may be mixed with a carrier, or diluted by a carrier, or enclosed within a carrier which may be in the form of a capsule, sachet, paper or other container. When the carrier is a diluent, it may be a solid, semisolid or liquid material which acts as a vehicle, excipient or medium for the inhibitor. Some examples of suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can also include lubricating agents, wetting agents, emulsifying agents, preservatives, and sweetening or flavoring agents.

Injectable preparations, for example, sterile injectable aqueous or oleaginous suspensions may be formulated according to the known art using suitable dispensing or wetting agents and suspending agents. The sterile injectable preparation can also be a sterile injectable solution or suspension in a nontoxic parenterally acceptable diluent or solvent, for example, as a solution in 1,3-butanediol.

The method described herein can be useful for treating cancers of a number of types, including but not limited to breast cancer, sarcomas and other neoplasms, bladder cancer, colon cancer, lung cancer, various leukemias and lymphomas. The cell lines used in the experiments discussed below include A431 human squamous carcinoma cells, MDA-MB-231 mammary carcinoma cells, HepG2 hepatoma cells, and HL-60 human promyelocytic leukemia cells. These cell lines are representative of mammary, esophogeal, prostate, head and neck and leukemia cancers found in human beings. However, it will be understood by those of skill in the art that the invention can also be practiced in veterinary applications.

EXAMPLES

Methods

Cell Culture: A431 human squamous carcinoma cells, HepG2 hepatoma cells and primary hepatocytes were maintained in RPMI-1640 media supplemented with 5% (v/v) fetal calf serum at 37° C. in 95% (v/v) air/5% (v/v) $CO_2$ (Schmidt-Ullrich et al. 1997 *Oncogene* 15, 1191–1197). For assessment of TUNEL and propidium iodide staining, cells were cultured for 4 days prior to radiation. For MTT assays on 96 well plates, cells were treated 2 days after plating.

The human promyelocytic leukemia cell line HL-60 was derived from a patient with acute promyelocytic leukemia. HL-60 cells were grown in complete RPMI-1640 medium (phenol red-free formulation) supplemented with 1.0% sodium pyruvate, non-essential amino acids, L-glutamine, penicillin and streptomycin and 10% heat-inactivated fetal bovine serum. Cultures were maintained at 37° C. in 95% (v/v) air/5% (v/v) $CO_2$. Cell densities were determined by Coulter counter, and basal cell viability assessed by vital dye-exclusion.

Radiation Treatment: For PD98059 treatment, the indicated concentrations of the drug in the culture media were obtained by addition from a 100 mM stock solution. The maximal concentration of carrier (DMSO) in the media was 0.02% (v/v). Cells were irradiated using a $^{60}$Co source at a dose rate of 1.8 Gy/min (Schmidt-Ullrich et al. 1997). Cells were maintained at 37° C. throughout the experiment except during the IR treatment itself Zero time is designated as the time point at which exposure to radiation ceased.

TUNEL Assays: TUNEL (Terminal Uridyl Nucleotide End Labeling) assays were used to quantitate double stranded DNA breaks as an indicator of cell survival after exposure to radiation. Cells were grown in 2-well glass chamber slides ($1\times10^5$ cells per well), and treated with varying concentrations of PD98059 30 minutes prior to irradiation. Control cells were treated with vehicle (DMSO) only. After irradiation, cells were fixed after either 24 or 48 hours. TUNEL was performed on the fixed cells as described by Jarvis et al. 1996, *J. Biol. Chem.* 271, 8275–8284. Randomly selected fields of fixed cells (n=5 per slide) were counted initially using propidium iodide counter stain, followed by examination and counting of TUNEL positive staining cells of the same field under FITC fluorescent light.

MTT Assays: MTT assays were used to measure the growth potential of cells after exposure to radiation. Cells were grown in 96-well plates (1000 cells per well) and 2 days after plating were pre-treated for 30 minutes with varying concentrations of PD98059/DMSO (control=DMSO only) before irradiation with 1 Gy IR. Cells were then cultured for a further 3–8 days. A 5 mg/ml stock solution of MTT reagent (3-[4,5-dimethylthiazol-2-yl]-2,5 diphenyltetrazolium bromide; thiazole blue) was prepared in DMEM media. For assay of mitochondrial dehydrogenase function, which has been correlated to clonal development, the MTT stock solution is diluted 1 to 10 in fresh media (DMEM+10% fetal calf serum) and 100 $\mu$l of this solution is added to each aspirated well of a 96-well plate. Cells are incubated for a further 3 hours at 37° C. MTT is converted into an insoluble purple formazan by cleavage of the tetrazolium ring by mitochondrial dehydrogenase enzymes (Carmichael et al. 1987, *Cancer Res.* 47, 943–946. After 3 hours, the media is aspirated and cells are lysed with 100 $\mu$l DMSO, releasing the purple product. Cells are incubated for a further 10 minutes at 37° C. with gentle shaking. Absorbance readings at 540 nm are determined using a computer controlled micro-plate analyser. The relationship between cell number and MTT absorbance/mitochondrial enzyme activity was linear over the range of 500–10,000 cells.

Test Exposures for ara-C and Taxol Studies: Cells in log phase growth were pelleted, rinsed twice in complete medium, resuspended at a density of $4\times10^5$ cells/ml, and maintained as indicated above (Cell Culture). Cells were exposed to test agents for appropriate intervals in complete medium; loss of cells under these conditions due to either washing or cell adherence was negligible ($\leq 5\%$). Test incubations were terminated with gentle pelleting of the cells by centrifugation at 400× g for 10 min. at 4° C. Following the determination of cell density, the cells were pelleted and prepared as outlined below for assays of DNA damage, assay of cloning efficiency, or assay of MAP kinase activity.

Quantitative Analysis of DNA Damage: The formation and release of DNA fragments and the corresponding breakage of bulk DNA were assessed by bisbenzamide spectrofluorophtometry. To measure intracellular DNA fragments, pelleted cells ($4\times10^6$ cells/pellet in quadruplicate) were resuspended in PBS and lysed by addition of 5 mM Tris-HCl, 30 mM EGTA, 30 mM EDTA, 0.1% Triton X-100, pH 8 (yielding a final density of $10^7$ cells,ml) with gentle mechanical agitation. The lysates were centrifuged at 30,000× g at 4° C. for 40 minutes. To measure extracellular DNA fragments, aliquots of incubation medium were adjusted to 5 mM Tris-HCl, 30 mM EGTA, 30 mM EDTA, pH 8 and centrifuged at 20,000× g at 4° C. for 40 min. The pellets were discarded and the presence of non-sedimenting DNA fragments in the supernatant from the lysate and medium extracts was quantified following dilution in modified Tris-sodium EGTA buffer (3 mM NaCl, 10 mM Tris- HCl, 1 mM EGTA, pH 8) by spectrofluorophotometry in the presence of Hoechst-33258 (1 μg/ml; μex=365, λem=460). Net fluorescence was directly proportional to the presence of DNA fragments; final values were calculated relative to a highly purified calf thymus DNA calibration standard, and are expressed as ng/μg DNA recovered or released from $10^6$ cells.

To measure corresponding loss of integrity of bulk DNA, pelleted cells ($8.25 \times 10^6$ cells/pellet in quadriplicate) were resuspended in cold PBS and subjected to timed alkaline denaturation in 0.1 N NaOH; denauration was terminated by neutralization in 0.1 N HCl. Cells were then further diluted in PBS and lysed by addition of 200 mM $K_2HPO_4$, 50 mM EDTA, 0.16% N-lauroylsarcosine with brief sonication. Damage to bulk DNA in cell lysates was quantified by spectrofluorophotometry in the presence of Hoechst-33258 (λex=350, λem=450). Net fluorescence was inversely proportional to introduction of strand breaks; final values were standardized against graded DNA strand breakage induced by scaled irradiation from a [$^{137}Cs$] point source (30 to 3000 rads), and are expressed as rad-equivalents.

Determination of Clonogenicity: Pelleted cells were rinsed extensively and prepared for soft-agar cloning. Cells were resuspended in cold PBS and seeded in 35-mm culture plates at a fixed density (400 cell/ml/well) in complete RPMI-1640 medium containing 20% fetal calf serum, 10% 5637-CM, and 0.3% Bacto agar. Cultures were mainatined for 10 to 12 days before formation of colonies (defined as groups of ≧50 cells) was scored.

Cytological Characterization of Apoptosis: Pelleted cells were resuspended in PBS and fixed in cytocentrifuged preparations. For visualization of apoptotic morphological alterations, fixed cells were stained with 20% Wright-Giemsa stain. At least 5 100-cell fields were scored for each treatment by conventional light miscroscopy by assessing the expression of cytoarchitectural characteristics of apoptosis (i.e. condensed nucleoplasm and cytoplasm, formation of membrane blebs, karyolytic degeneration of the nucleus into apoptotic bodies, and overall cell shrinkage). For visualization of apoptotic DNA damage, fixed cells were sequentially a) treated with ethanol-acetic acid (2:1, v/v) at 20° C. for 5 min, b) stained for broken DNA by treatment with terminal deoxynucleotidyl transferase (TdT) in the presence of fluorescein isothiocyanate (FITC)-dUTP at 37° C. for 60 min, and c) counterstained for intact DNA with 0.01% propidium iodide in sodium citrate at 20° C. for 10 min. At least 3 100-cell fields were scored for each treatment by fluorescent microscopy by assessing increased direct fluorescence of end-labeled double-stranded DNA.

Determination of MAPK Activity: Pelleted cells were rinsed in PBS, repelleted, and flash-frozen. Cell pellets were lysed in 25 mM Hepes, pH 7.4 containing 5 mM EGTA, 5 mM EDTA, supplemented with protease inhibitors (5 mM benzamidine, 1 mM phenylmethylsulfonylfluoride, 1 mg/ml soybean trypsin inhibitor, 40 μg/ml aprotinin, 1 μM microcystin LR) phosphatase inhibitors (0.5 mM trisodium orthovanadate, 0.5 mM tetrasodium pyrophosphate), and containing 0.056% sodium deoxycholate w/v, 1% Triton X-100 v/v, and 0.1% 2-mercaptoethanol v/v. Lysates were clarified by centrifugation at 5,000× g at 4° C. for 5 min. MAPK activity was assayed using MBP as a substrate following immunoprecipitation of p42/44 MAP kinase with protein A/agarose-conjugated antibody/antisera. Preimmune controls were also run to ensure selectivity of substrate phosphorylation. Reaction mixtures consisted of immuno-precipitated enzyme, substrate, and [γ-$^{32}$P] ATP (5000 Ci/pmol) in 25 mM Hepes, pH 7.4 containing 15 mM $MgCl_2$, 100 mM trisodium orthovanadate, 0.01% (v/v) 2-mercaptoethanol, 1 μM microstatin LR. Reactions were initiated by the addition of substrate. MAPK reactions were terminated by transfer to p81 filter paper; filters were rinsed repeatedly in 185 mM orhtophosphoric acid, and then dehydrated in acetone. Total radioactivity in filters was determined by liquid scintillometry.

EXAMPLE 1

Figure 1:
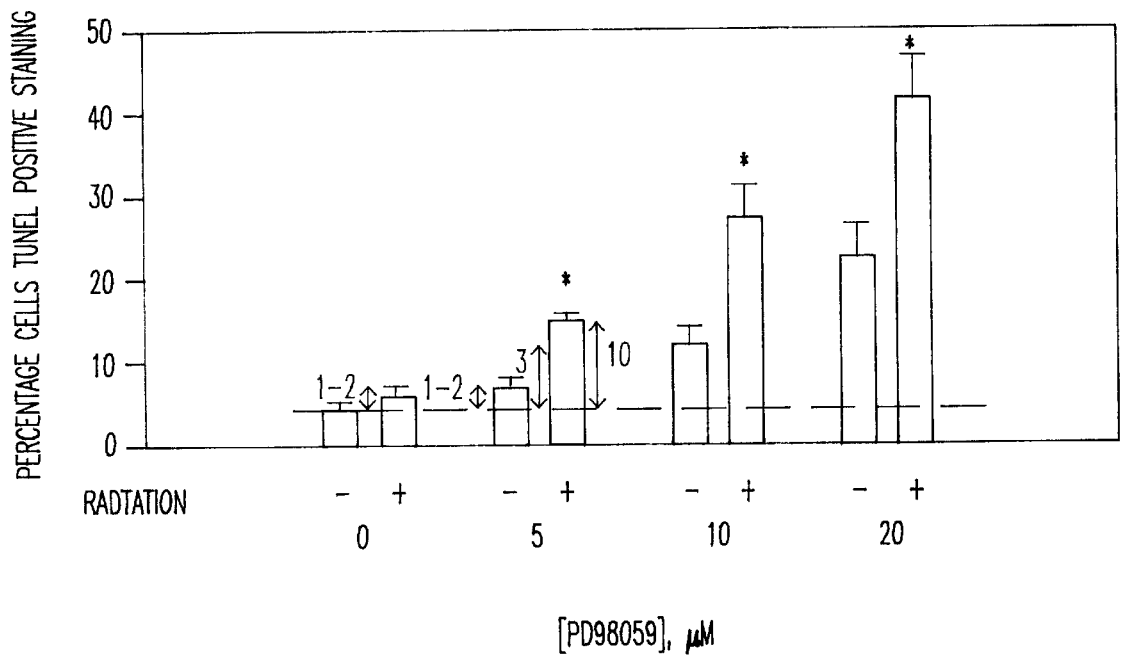
FIG. 1. TUNEL assays to assess the apoptosis response of A431 cells exposed to 1 Gy of radiation in the presence of varying PD98059 concentrations. Cells were pretreated with the indicated concentrations of PD98059 for 30 minutes prior to radiation exposure. Cells were exposed (+) or not (–) and TUNEL analysis was carried out as described in Methods and Example 1 below.
Figure 2:
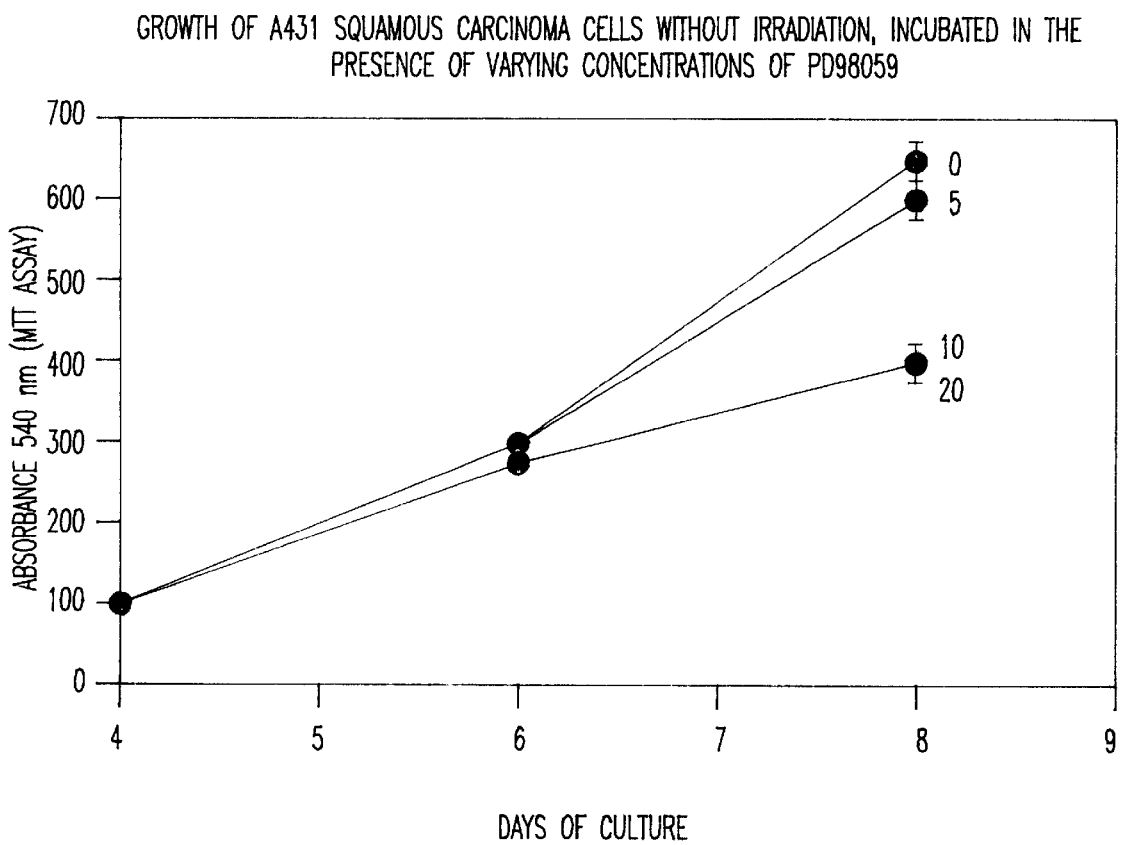
FIG. 2. Decreased proliferative rate of A431 cells in MTT assays over 4–8 days wherein cells were treated with PD98059 alone at the indicated concentrations. MTT assays were carried out as described in Methods and Example 1 below.

The following example shows that specific blockade of the p42/44 MAP kinase cascade function radio-sensitizes A43 1 cells. A43 Icells were were irradiated with 1 Gy in the presence of increasing concentrations of PD98059. The ability of cells to survive was assessed in three ways: first using TUNEL assays 24 hours after irradiation, second using propidium iodide staining for necrosis/cell integrity and third using MTT assays 4, 6 and 8 days after irradiation to determine growth potential. As can be seen in FIG. 1, at low concentrations of PD98059, a small non-significant detrimental effect was seen upon the basal levels of cell viability. Likewise, irradiation of cells with 1 Gy alone had little effect upon cell viability (FIG. 2; 0 μM PD98059). However, exposure of A431 cells to radiation in combination with PD98059 treatment caused a large potentiation of cell death as judged in both TUNEL asssays (FIG. 2; lanes corresponding to 5, 10 and 20 μM PD98059) and by propidium iodide staining of unfixed cells (not shown). For example, a single 1 Gy exposure plus 5 μM PD98059 treatment tripled the amount of cell killing compared to the amount induced by either treatment alone, and quantitatively increased the percentage of cells exhibiting double stranded DNA breaks from ~4–15%. Indeed, the enhancement ratios for radiation plus PD98059 co-treatment versus either radiation exposure or PD98059 treatment alone were increased approximately threefold, as can be seen by comparing the values obtained at 5 μM PD98059 in FIG. 2. Three times more killing was observed than would be expected based on simple additivity of killing by the drug alone plus killing by radiation alone. In all instances examined, the dose dependent ability of PD98059 treatment to inhibit the activity of the p42/44 MAP kinase cascade correlated with its dose-dependent ability to potentiate cell death after irradiation with 1 Gy.

Figure 3:
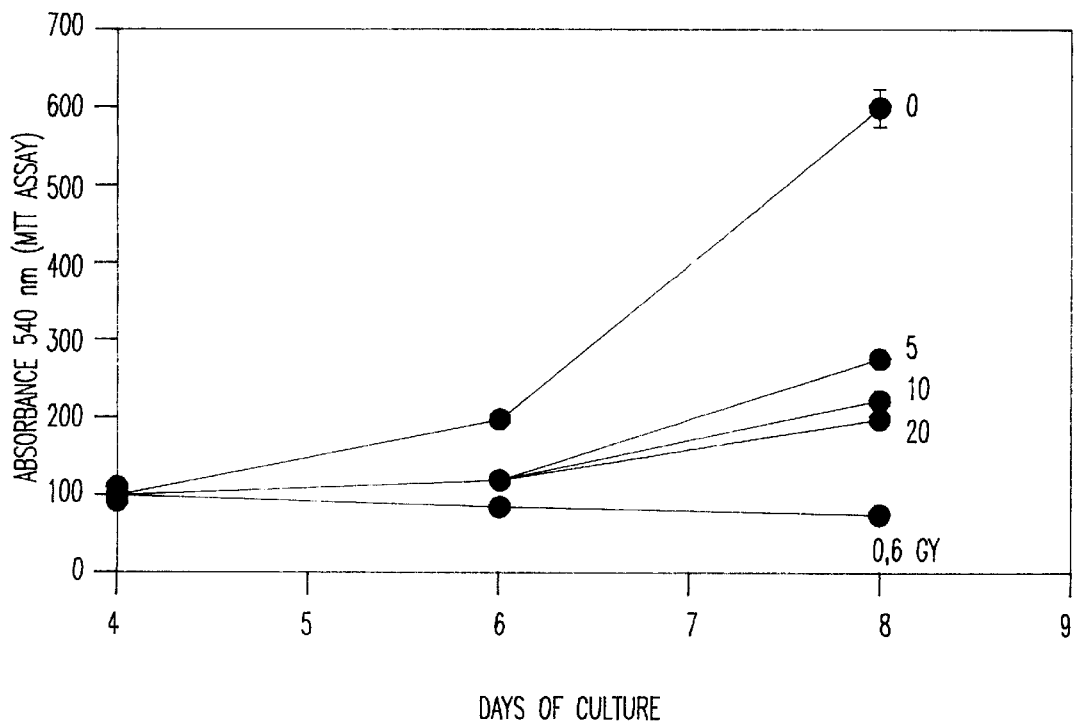
FIG. 3. Decreased proliferative rate of A431 cells in MTT assays over 4–8 days wherein cells were treated with PD98059 and exposed to 1 Gy radiation. Cells were pretreated with PD98059 at the indicated concentrations 30 minutes prior to radiation exposure and cultured 4–8 days in the presence of PD98059. Cells exposed to 6 Gy without PD98059 treatment are also indicated on the graph.

The ability of radiation exposure and PD98059 treatment of cells to potentiate a reduction in cell number/proliferation capacity as judged using MTT assays between 4–8 days after irradiation was also determined. As can be seen in FIG. 3, exposure of A431 cells to radiation and PD98059 treatment caused a large reduction in proliferative capacity over either exposure alone or treatment alone. Irradiation with 1 Gy alone had little effect on proliferative capacity whereas irradiation with 1 Gy in combination with 5, 10 or 20 μM PD98059 markedly decreased cellular proliferation. Irradiation with 6 Gy appeared to abolish proliferation over the time period examined. Thus, in agreement with the TUNEL assay data presented above, increased enhancement ratios of at least threefold were observed. Treatment of A431 cells with PD98059 alone also resulted in an overall dose-dependent decrease in proliferative capacity over 96 hours as judged by a reduction of [$^3$H]thymidine incorporation into DNA (not shown), demonstrating by an independent methodology that blockade of MAP kinase function by PD98059 treatment decreases proliferative capacity. Thus, this example demonstrates that a dose-dependent inhibition of the p42/44 MAP kinase cascade by PD98059 reduces both overall proliferative potential and potentiates the ability of radiation to kill A431 human squamous carcinoma cells.

EXAMPLE 2

Figure 4:
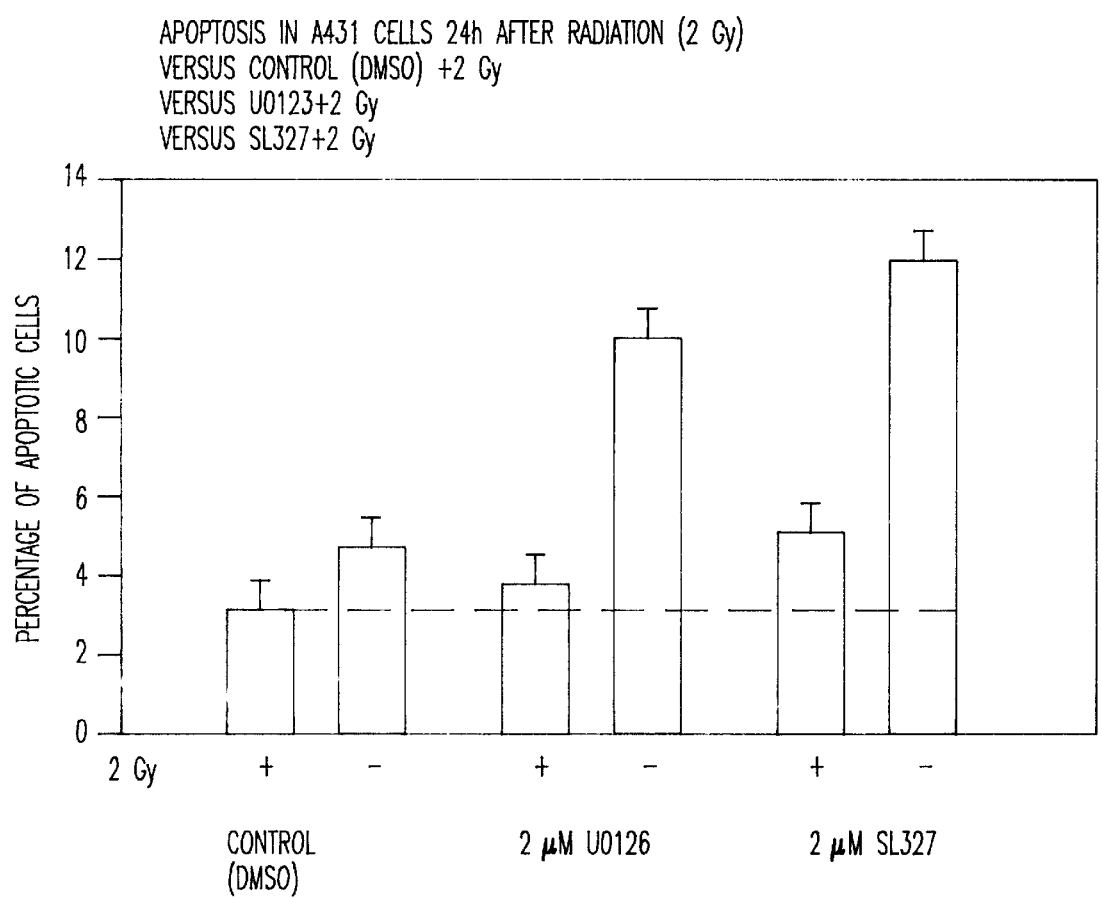
FIG. 4. TUNEL assays to assess the apoptosis response of A431 cells exposed to 2 Gy of radiation in the presence of vehicle (DMSO), 2 μM U0126 or 2 μM SL327. Cells were pretreated with 2 μM inhibitor for 30 minutes prior to radiation exposure. Cells were exposed (+) or not (−) and TUNEL analysis was carried out as described in Methods and Example 1 below.

The following example demonstrates that two other compounds that specifically inhibit the p42/44 MAP kinase cascade also radio-sensitize A431 cells. A431 cells were irradiated with 2 Gy in the presence of 2 $\mu$M U0126 or 2 $\mu$M SL327. The ability of the cells to survive was assessed using TUNEL assays 24 hours after irradiation and the results are depicted in FIG. 4. As can be seen, the presence of either of the specific p42/44 MAP kinase cascade inhibitors caused a dramatic increase in the percentage of apoptotic cells.

Figure 5:
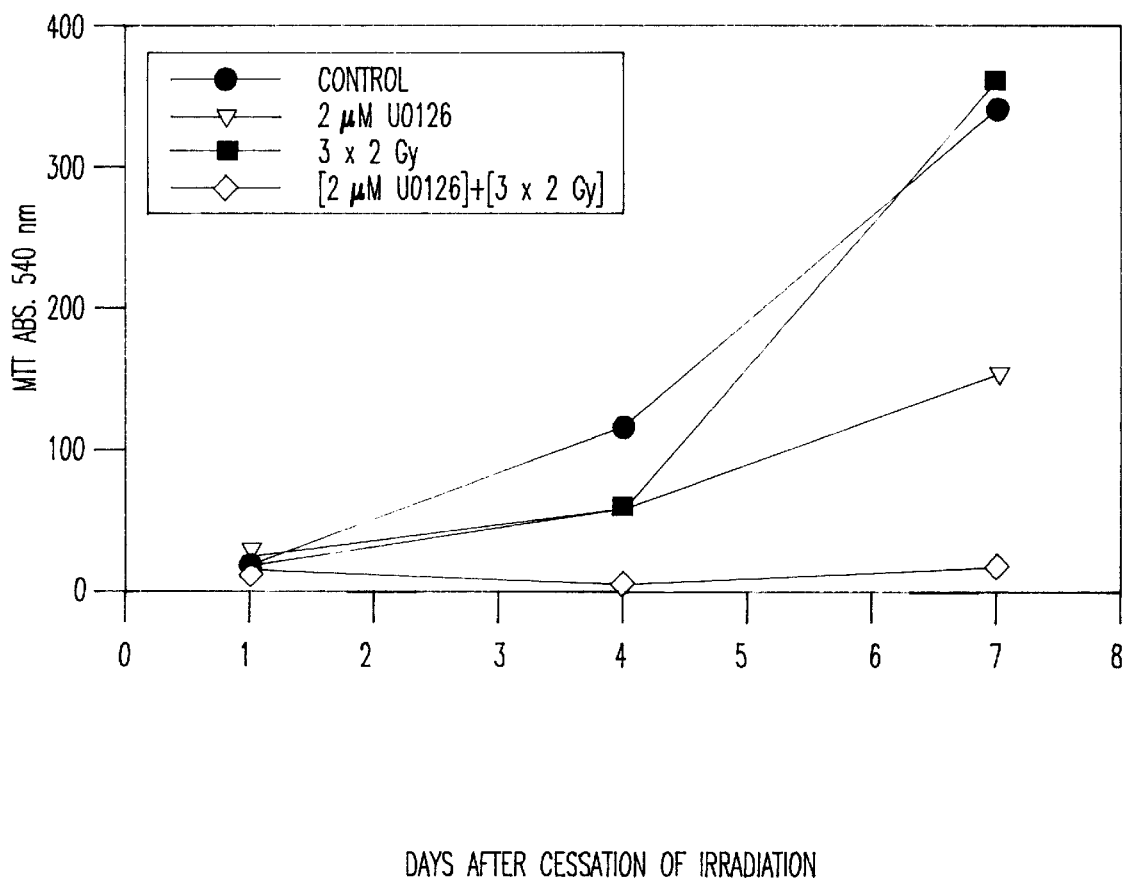
FIG. 5. Decreased proliferative rate of A431 cells in MTT assays over 4–8 days wherein cells were treated with radiation (3×2 Gy) alone, 2 μM U0126 alone, or radiation plus U0126. Control cells were treated with vehicle (DMSO).

The ability of the inhibitor U0126 to potentiate a reduction in cell number/proliferation capacity of A431 cells as judged using MTT assays was also determined. The results are presented in FIG. 5. The combination of U0126 (2 $\mu$M) plus exposure to radiation (3×2 Gy) was markedly more effective in abolishing cellular proliferation than either treatment with U0126 alone or irradiation alone. This data is in accord with the TUNEL assay data presented above.

To further extend these investigations, the efficacy of U0126 was tested in the mammary cancer cell line MDA-MB-23 1. As described in the previous experiment, cells were exposed to 2 $\mu$M U0126 alone, radiation (3×2 Gy) alone, or to the combination of U0126 plus radiation. Control cells were treated with vehicle alone. The results of the MTT assays, depicted in FIG. 6, showed that, again, the combination of the specific p42/44 MAP kinase cascade proper inhibitor U0126 plus radiation was far more effective in decreasing cellular proliferative potential than either treatment alone. This experiment indicates that the radiosensitizing effect of the p42/44 MAP kinase cascade proper inhibitor U0126 is not confined to A431 cells but also extends to mammary cancer cells.

EXAMPLE 3

The following example demonstrates that the radiosensitization of cells via inhibition of the p42/44 MAP kinase cascade is restricted to proliferating cell types whereas slowly growing cell types are spared. This is highly relevant because the neoplastic cells which are targeted for destruction by radiation therapy are rapidly proliferating, in contrast to most normal slowly growing somatic cells. Primary hepatocytes (representing slow growing "normal" cells) and HepG2 hepatoma cells derived from a cancerous cell line were cultured under identical conditions. Control cells of both types were left untreated. Matched samples of both cell types were treated with the p42/44 MAP kinase cascade inhibitory drug SL327, or exposed to radiation (2×2 Gy), or treated with SL327 and exposed to radiation. Twelve hours after the final irradiation, cells were processed and the number of dead (apoptoic) cells was determined by the TUNEL assay. The results are shown in FIG. 7. As can be seen, the slowly growing primary hepatocytes are fairly resistant to combined drug/radiation therapy. In contrast, the more rapidly growing hepatoma cells are effectively killed by the combination of drug and radiation treatment. The combination of radiation plus SL327 resulted in an approximately 2.5-fold increase in cell killing of rapidly growing cells, compared to radiation alone. This study confirms that the combination of radiation plus MAP kinase "proper" specific inhibitor is significantly more effective in inducing apoptosis than radiation alone. Furthermore, the effect is specific for rapidly growing cells.

EXAMPLE 4

The following Example demonstrates that PD-98059 is also effective in potentiating the apoptotic activity of the chemotherapeutic agents ara-C and taxol. HL-60 cells were exposed to ara-C in the absence or presence of PD98059. Following this treatment, the cells were eveluated for MAP kinase activity, DNA strand breakage, clonogenicity potential and extent of apoptosis. As can be seen in FIG. 8, acute exposure to PD 98059 over a broad range of concentrations (1–100 $\mu$M) resulted in a pronounced concentration-related decline of basal MAP kinase activity (decreased maximally by $\geq$65%, with an $EC_{50}$ of $\leq$5 $\mu$M). Note that the sublethal concentration of 5 $\mu$M PD 98059 completely suppresses drug-related stimulation of MAP kinase by ara-C.

As seen in FIG. 9a, the amount of DNA strand breakage induced by ara-C was substantially increased by the presence of PD98059. In addition, FIG. 9b shows the extent of apoptosis attributable to ara-C action was dramatically increased in the presence of PD98059, and the clonogenic potential of the HL-60 cells was practically nullified in the presence of the two agents, even though neither alone had this effect. These obsevations demonstrate that the specific p42/44 MAP kinase cascade proper inhibitor PD98059 is highly effective in potentiating the apoptotic activity of the chemotherapeutic agent ara-C.

The effects of PD98059 were also examined with respect to modulation of taxol-mediated apoptosis in HL-60 cells. As can be seen in FIG. 10, exposure to PD98059 (10 $\mu$M) for 15 hours induced apoptosis in a small percentage of cells (~6–7 %) but increased taxol-mediated cell death substantially, from ~27% to 58%.

These four Examples demonstrate that inhibitors which are specific for the p42/44 MAP kinase cascade "proper", when used in combination with radiation or chemotherapy agents, enhance the radiation- or chemotherapy-induced apoptosis of cancer cells. Furthermore, with respect to radiation, the effect is specific for rapidly dividing cells. Results essentially identical to those obtained in Example 1 were also obtained using RT2 rat glialblastoma cells, DU47 prostate cancer cells and HL-60 promyoleukemic cells (data not shown).

The radiation experiments were thus performed in six different cancer cell lines and three different inhibitors specific for the p42/44 MAP kinase cascade proper were utilized. The chemotherapy experiments were performed using two different chemotherapeutic agents.

While the results show the use of three agents which inhibit the ability of Raf to phosphorylate and activate MEK1 and MEK2, similar results would be expected with other agents which inhibit other steps in the p42/44 MAP kinase cascade proper shown in Pathway 1. We note that the inhibitors PD98059, U0126 and SL327 all inhibit MEK1 and MEK2 and all cause radiosensitization of cancer cells. Yet they are chemically dissimilar. Their ability to radiosensitize is likely to be based solely on their ability to inhibit the cascade, rather than on some other feature. Thus it is expected that other inhibitors specific for this cascade will also cause radiosensitization.

While the invention has been described in terms of its preferred embodiments, the invention can be practiced with modification and variation within the spirit and scope of the appended claims.

We claim:

1. A method for enhancing the killing of cancer cells, comprising the steps of:
   sensitizing said cancer cells by exposing them to an inhibitor that is specific for any step of the p42/44 MAP kinase cascade proper, and
   exposing said cancer cells to a lethal agent selected from the group consisting of taxanes, heat, electrical fields, pH extremes, magnetic fields and radiant energy including ionizing radiation, ultraviolet light and high intensity red light.

2. The method of claim 1 wherein said sensitizing step comprises the step of administering said inhibitor to a patient with said cancer cells.

3. The method of claim 1 wherein said inhibitor inhibits the ability of Raf to phosphorylate and activate the enzymes MEK1 and MEK2.

4. The method of claim 3 wherein said inhibitor is selected from the group consisting of PD98059, PD184352, U0126, SL327, and SW073.

5. A method of treating cancer in mammals, comprising the steps of administering to a patient in need thereof an effective amount of an inhibitor specific for the p42/44 MAP kinase cascade proper, and providing said patient with radiation therapy.

6. The method of claim 5 wherein said step of administering said effective amount of an inhibitor specific for the p42/44 MAP kinase cascade proper is carried out prior to said radiation therapy.

7. The method of claim 5 where in said step of administering said effective amount of an inhibitor specific for the p42/44 MAP kinase cascade proper is carried out simultaneously with said radiation therapy.

8. The method of claim 5 wherein said step of administering said effective amount of an inhibitor specific for the p42/44 MAP kinase cascade proper is carried out after said radiation therapy.

9. The method of claim 5 wherein said inhibitor specific for the p42/44 MAP kinase cascade proper inhibits the ability of the Raf protein kinases to phosphorylate and activate the enzymes MEK1 and MEK2.

10. The method of claim 9 wherein said inhibitor is selected from the group: PD98059, PD184352, U0126, SL327 and SW073.

11. The method of claim 5 wherein said step of administering is oral.

12. The method of claim 5 wherein said step of administering is perenteral.

13. A method of treating cancer in mammals, comprising the steps of administering to a patient in need thereof an effective amount of an inhibitor specific for the p42/44 MAP kinase cascade proper, and providing said patient with a taxane.

14. The method of claim 13 wherein said step of administering said effective amount of an inhibitor specific for the p42/44 MAP kinase cascade proper is carried out prior to said step of providing said taxane, and wherein said taxane is taxol.

15. The method of claim 13 wherein said step of administering said effective amount of an inhibitor specific for the p42/44 MAP kinase cascade proper is carried out simultaneously with said step of providing said taxane, and wherein said taxane is taxol.

16. The method of claim 13 wherein said step of administering said effective amount of an inhibitor specific for the p42/44 MAP kinase cascade proper is carried out after said step of providing said taxane, and wherein said taxane is taxol.

17. The method of claim 13 wherein said inhibitor specific for the p42/44 MAP kinase cascade proper inhibits the ability of the Raf protein kinases to phosphorylate and activate the enzymes MEK1 and MEK2.

18. The method of claim 17 wherein said inhibitor specific for the p42/44 MAP kinase cascade proper is selected from the group: PD98059, PD184352, U0126, SL327 and SW073.

19. The method of claim 13 wherein said step of administering is oral.

20. The method of claim 13 wherein said step of administering is perenteral.

* * * * *

UNITED STATES PATENT AND TRADEMARK OFFICE
CERTIFICATE OF CORRECTION

PATENT NO.    : 6,147,107
DATED         : Nov. 14, 2000
INVENTOR(S)   : Dent and Grant It is certified that error appears in the above-identified patent and that said Letters Patent are hereby corrected as shown below:

[75] Inventors: Paul Dent, Glen Allen; Steven Grant; Richmond, both of VA Signed and Sealed this First Day of May, 2001

Attest:

NICHOLAS P. GODICI

Attesting Officer        Acting Director of the United States Patent and Trademark Office